United States Patent [19]

Jacob-LaBarre

[11] Patent Number: 5,192,315
[45] Date of Patent: Mar. 9, 1993

[54] TOTAL OCULAR REPLACEMENT APPARATUS WITH MUSCLE ATTACHMENT SITES

[76] Inventor: Jean T. Jacob-LaBarre, 135 Arlington Dr., Metairie, La. 70001

[21] Appl. No.: 856,465

[22] Filed: Mar. 24, 1992

[51] Int. Cl.$^5$ .............................................. A61F 2/14
[52] U.S. Cl. ........................................................ 623/4
[58] Field of Search ............................................ 623/4–6

[56] References Cited

U.S. PATENT DOCUMENTS

| | | | |
|---|---|---|---|
| 2,516,804 | 7/1950 | Rolf et al. | 3/13 |
| 2,571,721 | 10/1951 | Jardon | 623/4 |
| 2,617,994 | 11/1952 | Noelle | 623/4 |
| 2,629,877 | 3/1953 | Jardon et al. | 3/13 |
| 2,649,590 | 8/1953 | Cutler | 3/13 |
| 2,653,327 | 9/1953 | Allen et al. | 3/13 |
| 2,660,732 | 12/1953 | Stone, Jr. | 3/13 |
| 2,661,480 | 12/1953 | Rosen et al. | 623/4 |
| 2,667,645 | 2/1954 | Moulton | 3/13 |
| 2,688,139 | 9/1954 | Jardon | 3/13 |
| 4,955,909 | 9/1990 | Ersek et al. | 623/11 |
| 5,026,392 | 1/1991 | Gordon | 623/4 |

*Primary Examiner*—David Isabella
*Assistant Examiner*—Dinh X. Nguyen
*Attorney, Agent, or Firm*—Pravel, Gambrell, Hewitt, Kimball & Krieger

[57] ABSTRACT

An orbital implant and conformer affords mobility and decreases the likelihood of implant extrusion and the "dropped socket" appearance. The implant device consists of a spherical implant whose circumference is dotted with a cellular ingrowth surface to which all the remaining ocular muscles can adhere and act upon. A shaft protrudes anteriorly from the implant through the conjunctival sheath into the front orbital space. The base of the shaft and the area of the implant encircling the shaft also have a cellular ingrowth surface into which the conjunctiva can grow forming a tight seal. The shaft fits into a corresponding small hole in the conformer. The shaft communicates the muscular movement of the implant directly to the conformer. Since the conformer sits on the shaft, its weight is more evenly distributed throughout the orbital socket and should not distend the eyelids. The cellular ingrowth areas on the implant, on and around the base of the shaft, and at the muscle junctions, cause a close apposition of the tissues to the implant that prohibits implant migration and extrusion.

45 Claims, 3 Drawing Sheets

SUPERIOR VIEW

INFERIOR VIEW

ANTERIOR VIEW

TOTAL OCULAR REPLACEMENT APPARATUS WITH MUSCLE ATTACHMENT SITES

BACKGROUND OF THE INVENTION

1. Field Of The Invention

The present invention relates to medical prosthetic devices and more particularly relates to an improved ocular prosthetic device having improved tissue compatibility and attachment. Even more particularly, the present invention relates to an improved total ocular replacement that has muscle attachment sites upon the surface of a polymeric implant, the attachment sites in between the remaining outer surface coating that discourages muscle attachment.

2. General Background

Current ocular replacement implants and conformers often produce ocular complications and cosmetic defects, such as a sagging lower eyelid, poor movement relative to the fellow eye, implant extrusion or migration as well as potentially fatal orbital infections.

Prior total ocular replacement prosthetic devices have generally consisted of non-biocompatible materials that do not adequately interface between the implant and the surrounding muscles and tissues. Metal meshes, prongs, clamps, clips and pins allow significant mechanical erosion between the implant and tissues due to physical compliance differences.

Prior art devices generally suffer from a lack of selective ingrowth when a biocompatible material is used in the implant design. Muscles and tissues adjacent to a biocompatible porous material (whether synthetic or donor tissue) will indiscriminately ingrow and scar down on to it. The scarring and ingrowth can constrict the movement of the implant. This also produces a problem if the implant needs to be removed at a future date for medical reasons. In many cases the prosthesis cannot be removed without removing a significant amount of muscular tissue as well.

Other devices suffer from a lack of an implant design that has the biomechanics to move the implant in a natural appearing way. To do so all the extra-ocular muscles should be attached to the prosthesis in their anatomically correct positions.

Another problem of prior art total ocular replacements is a lack of adequate co-operative movement of the cosmetic conformer with the follow eye. To have this there should be a direct connection between the cosmetic conformer and the implant. All designs that have any such connection do not have an effective method of keeping the conjunctiva closed around the connection. In addition, wear on the unsecured conjunctiva at the connection point produces thinning and retraction of it thereby providing an entrance for pathogens into the orbital space.

A number of prior art devices have been disclosed in patents. These patents have dealt with the need to attach the extra-ocular muscles which have been removed from the diseased eye to the circular-shaped implant replacing the eye. The attachment is necessary for the two reasons: 1) to help anchor the implant into the orbit and 2) to transmit movement to the implant so that it can respond similarly as the eye did. However, prior art designs generally have attachment means for only the four (4) rectus muscles and do not include the two oblique muscles. In addition, the attachment means while varying in style result in several detrimental conditions for the muscles.

Patents by Rolf (U.S. Pat. No. 2,516,804), Rosen (U.S. Pat. No. 2,661,480) and Cutler (U.S. Pat. No. 2,649,590) all teach the use of a ring (generally metal) that the muscles are wrapped and sutured around. This type of attachment means creates friction and wear on the muscles where the ring rubs against them.

The Allen et al. patent (U.S. Pat. No. 2,653,327) teaches imbricating the muscles over the anterior area of the implant. Imbrication (overlapping the tendinous ends of two opposing muscles and suturing them together such that the four rectus muscles are sutured together in a roman cross shape) results in the four rectus muscles scarring down together into one larger mass anterior to the implant which severely restricts their range of motion.

Patents issued to Stone (U.S. Pat. No. 2,660,732), Jardon (U.S. Pat. No. 2,571,721), and Moulton (U.S. Pat. No. 2,667,645) all use a metal mesh over the entire anterior portion of the implant which the muscles are attached to by sutures and various metal clips.

Jardon (U.S. Pat. No. 2,629,877), Noelle (U.S. Pat. No. 2,617,994) and Gordon (U.S. Pat. No. 5,026,392) all disclose the use of synthetic tabs of the ends of the muscles to act as the attachment means to the implant. Jardon '877 sutures the muscles to metal clips which fit into tunnels in the implant; Noelle '994 uses all metal meshes and clips; Gordon '392 uses both synthetic polymers and metals. Gordon's muscles attachment sites are movable in only one plane of the implant.

The Clarke U.S. Pat. No. 2,634,423 uses horizontal and vertical metal pins to keep the muscles in place.

Jardon (U.S. Pat. No. 2,688,139) describes a completely porous implant. However, this construction allows for scarring cellular attachment along the entire length of the muscles attached restricting their strength and range of motion.

Jardon '139 and '721 and Cutler '590 describe the use of a shaft protruding out of the implant for use of transmitting the implants motion to the cosmetic conformer. Cutler's patent uses a detachable pin that is inserted post-operatively into the implant and the rear of the conformer. The Jardon U.S. Pat. Nos. 2,571,721 and 2,629,877 each disclose an attached shaft that protrudes from the implant; however, it does not have porous material on the shaft itself for close apposition of the conjunctiva.

SUMMARY OF THE PRESENT INVENTION

The present invention provides an improved implant/conformer design for replacement of a patient's diseased eyeball. The implant of the present invention may be secured in place by all of the extra-ocular muscles, Tenon's capsule, and conjunctiva with a biocompatible interface.

The present invention thus provides an implant that allows a water tight seal between the conjunctiva and the implant to act as a barrier to infection.

During surgical implantation, once the patient is sedated and the eye is anesthetized, the attaching muscles and tissues are dissected completely away from the patient's diseased natural eyeball. The conjunctiva and Tenon's capsule are incised down to the sclera as close as possible to the cornea a full three hundred and sixty (360) degrees. The extra-ocular muscles are disinserted at the point of their insertion on the sclera. The optic nerve is severed and the eye removed.

Once the bleeding is controlled, the implant is inserted into the cone formed by the extra-ocular muscles. All the muscles are then attached to the biocompatible patches or pads corresponding to their correct anatomical positions with non-absorbable suture. The position of the implant is checked with the fellow eye and the muscles re-positioned on the pads in any direction.

The Tenon's capsule and conjunctiva are closed up around the shaft and sutured with resorbable suture to the pads around the base of the shaft and on the shaft itself. The orbit is allowed to heal before a cosmetic conformer is fit. A mold of the pre-conjunctival space is taken to insure the fit of the cosmetic conformer on to the shaft. Any time post-operatively the conjunctiva may be opened and the muscles re-positioned on the patches if the implant becomes skewed or out of alignment with the fellow eye.

If due to uneven healing, scarring, or atrophy of the muscles and orbital tissues the implant becomes so severely unaligned the conformer can not be inserted and removed easily, the shaft of the implant can be cut off at its base just above the encircling ingrowth pad. The ingrowth pad formerly around the shaft itself may be trimmed and glued over the remaining shaft stump. The conjunctiva may then be re-closed completely over the stump. The resulting raised area will not interfere with insertion and removal of the conformer but will still be able to communicate movement between the implant and conformer.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
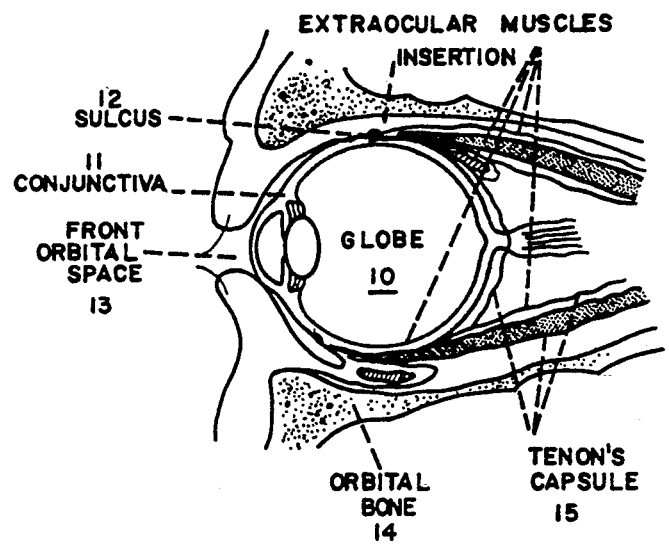
FIG. 1 is a sectional anatomical side view of the orbit and its contents.

FIG. 1 illustrates generally a side sectional anatomical view of a patient's eye. Shown in FIG. 1 is the ocular globe 10 and conjunctiva 11, sulcus 12, front orbital space 13, orbital bone 14, and Tenon's capsule 15. Thus, FIG. 1 illustrates the orbit and its contents prior to surgery.

Figure 2:
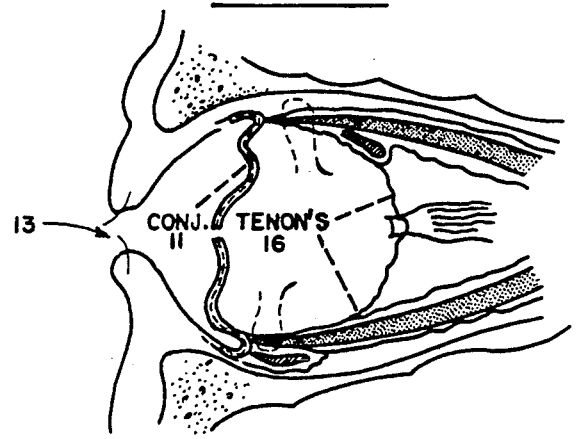
FIG. 2 is a side schematic view of the orbit after enucleation.

FIG. 2 illustrates the orbit after enucleation. In FIG. 2, the conjunctiva 11 and Tenon's 16 are shown, the globe having been removed.

Figure 3:
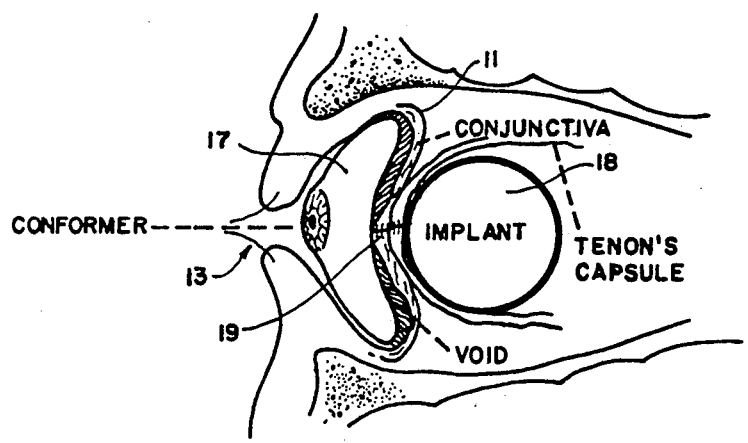
FIG. 3 is a side sectional view illustrating a typical total ocular implant article after placement in the orbit.

In FIG. 3, a prior art type implant is illustrated having a conformer 17 and ocular implant 18. Suture 19 secures the conjunctiva and ocular muscle tissue at 19 to the rear of the conformer 17 and to the front or anterior surface of the implant 18.

Figure 4:
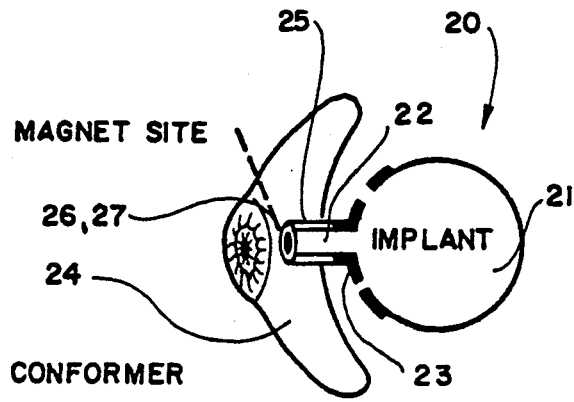
FIG. 4 is a side schematic view of the article of the present invention.

In FIG. 4, the preferred embodiment of the total ocular implant of the present invention is shown, designated generally by the numeral 20. Ocular prosthesis 20 includes a spherically shaped portion 2 connected to forwardly extending post 22 which can be cylindrical. The joint 23 between post 22 and spherical portion 21 can be an integral connection. A conformer 24 is positioned forwardly of the spherical portion 20. Conformer 24 has a socket 25 on its rear concave surface receptive of post 22. The post 22 carries a magnetic member 26. Similarly, the conformer 24 has a magnetic member or a metallic member 27 so that a magnetic field secures the post to the conformer with a removable connection.

Figure 5:
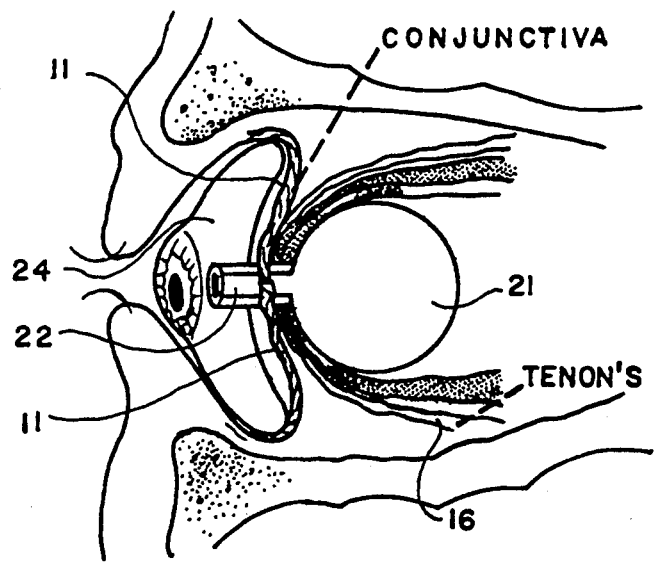
FIG. 5 is a side schematic view of the implant article of the present invention after placement into the orbit.

The spherical portion 21, post 22, and conformer 24 are illustrated in position in FIG. 5.

Figure 6:
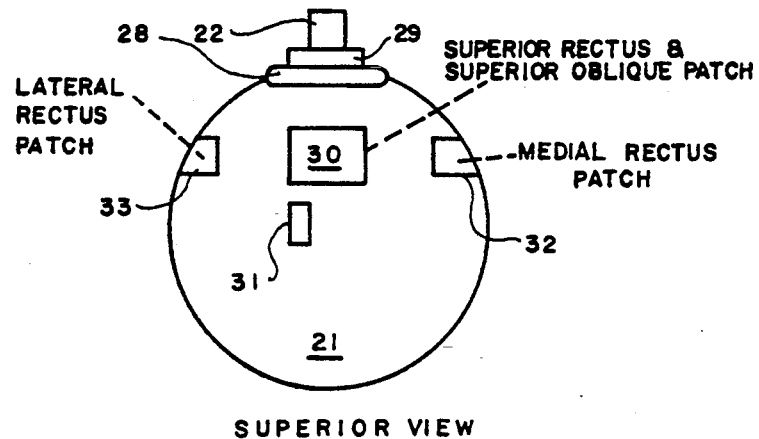
FIG. 6 is a superior view of the total ocular replacement article of the present invention illustrating muscle attachment sites.
Figure 7:
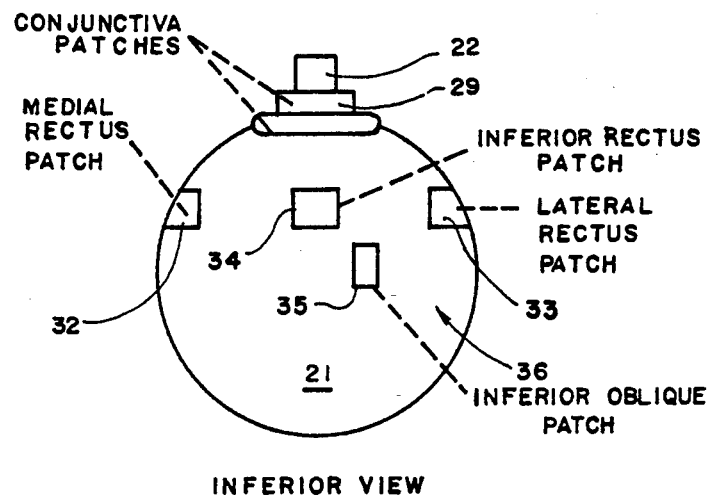
FIG. 7 is an inferior view of the total ocular replacement article of the present invention illustrating muscle attachment sites.
Figure 8:
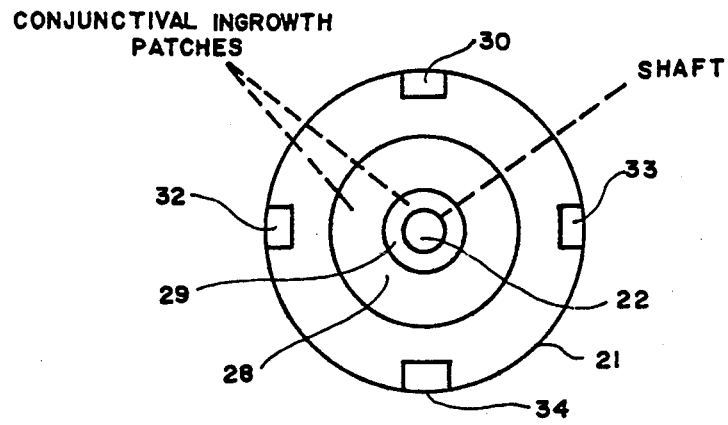
FIG. 8 is an anterior view of the total ocular replacement article of the present invention illustrating muscle attachment sites.

FIGS. 6, 7, and 8 illustrate muscle attachment sites and cell ingrowth areas on the surface of the ocular prosthesis 20. A first annular cell ingrowth patch 28 is supplied on the anterior surface of spherical portion 21 of the prosthesis 20. The cell ingrowth patch 28 can be, for example, porous silicone. The base of post 22 is also provided with an annular cell ingrowth patch 29. Annular cell ingrowth patch 29 extends from the joint 23 between post 22 and sphere 21 and forwardly portion of post 22. The combination of annular cell ingrowth patches 28, 29 ensures that ocular tissue will attach to both the anterior surface of the spherical portion 21 of ocular prosthesis 20, and the joint 23 between post 22 and spherical portion 21 as well as a portion of post 22 adjacent joint 23.

Muscle attachment sites in the form of porous patches are provided as shown in FIGS. 6, 7, and 8. In the superior or top view of FIG. 6, superior rectus attachment site 30 and superior oblique attachment site 31 are shown on the upper surface of the ocular prosthesis 20. Also shown in FIG. 6 are portions of medial rectus patch 32 and lateral rectus patch 33.

In the inferior or bottom view of prosthesis 20 as shown in FIG. 7, medial rectus patch 32 and lateral rectus patch 33 are partially shown, i.e., the remainder of the patch 32 and 33 respectively which are not seen in FIG. 6. Thus, the patches 32, 33 could be rectangularly shaped as with regard to the superior rectus patch 30.

Also shown in the inferior or bottom view of FIG. 7 are inferior rectus patch 34 and inferior oblique patch 35. Each of the patches 30–35 thus defines muscle attachment sites on the outer surface 36 of spherical portion 21. This outer surface 36 is preferably a surface that discourages muscle attachment. In this fashion, the ocular muscle tissue will only attach at a desired site rather than at locations all over the outer surface 36 of spherical portion 21. In this fashion, the attachments of particular ocular muscles to particular locations is controlled with porous tissue ingrowth sites.

In the preferred embodiment, the implant spherical portion 21 is preferably polymeric. The spherical implant portion 21 can be, for example, of a silicone polymer material or like synthetic polymer material.

In the preferred embodiment, the annular cell ingrowth areas 28, 29 and the muscle attachment sites 30–35 are of a porous or micropillared polymeric material such as, for example, porous silicone and having a pore size of at least 20 microns. If a micropillared polymer is used, such a polymer patch would have a cubic array of micropillars of at least 20 microns. The muscle attachment surfaces can be polyurethane, polyester, polytetrafluoroethylene. The muscle attachment surfaces can be woven or expanded polytetrafluoroethylene.

The orbital implant 20 as aforedescribed affords improved mobility and decreases the likelihood of implant extrusion and the "dropped socket" appearance. During use, the shaft 22 portion protrudes anteriorly from the spherical implant portion 21 through the conjunctival sheath into the front orbital space 13. The shaft 22 communicates the muscular movement of the spherical implant portion 21 directly to the conformer 24. Since the conformer 24 sits on the shaft 22, its weight is more evenly distributed throughout the orbital socket and thus should not distend the patient's eyelids. The cellular ingrowth areas 28, 29 cause a close apposition of the tissues to the implant that prohibits implant migration and extrusion.

During surgical implantation, the conjunctiva 11 is incised away from the patient's diseased natural eyeball 10 a full 360°. The conjunctiva 11 and Tenon's capsule 15 are dissected completely away from the globe 10. The extra ocular muscles are disinserted at the point of their insertion on the sclera. The optic nerve is severed and the ocular globe 10 removed. Once bleeding is controlled, the implant spherical portion 21 is inserted into the cone formed by the ocular muscles. All of the ocular muscles are then attached to the biocompatible muscle attachment sites 30, 35 and corresponding to their correct anatomical positions using non-absorbable suture. The position of the implant 20 is then checked with the patient's other eye. The muscles can be repositioned upon the pads in any desired direction in order to correct for any error. The Tenon's capsule 16 and conjunctiva 11 are closed up around the shaft 22 and sutured with resorbable suture to the cellular ingrowth areas 28, 29 around the base of the shaft and on the shaft itself respectively. The orbit is allowed to heal before a cosmetic conformer 24 is fitted. The mold of the preconjunctival space is taken to ensure fit of the cosmetic conformer onto the shaft 22. Any time post operatively, the conjunctiva 11 may be opened and the muscles repositioned on the patches if the implant spherical portion 21 becomes skewed or out of alignment with the patient's other eye.

The following table lists the part numbers and part descriptions as used herein and in the drawings attached hereto.

TABLE 1

| Part Number | PARTS LIST Part Description |
|---|---|
| 10 | globe |
| 11 | conjunctiva |
| 12 | sulcus |
| 13 | orbital space |
| 14 | orbital bone |
| 15 | Tenon's capsule |
| 16 | Tenon's |
| 17 | conformer |
| 18 | ocular implant |
| 19 | suture |
| 20 | ocular prosthesis |
| 21 | sphere |
| 22 | post |
| 23 | joint |

TABLE 1-continued

| Part Number | PARTS LIST Part Description |
|---|---|
| 24 | conformer |
| 25 | socket |
| 26 | magnet |
| 27 | magnet |
| 28 | annular cell ingrowth patch |
| 29 | annular cell ingrowth patch |
| 30 | superior rectus attachment site |
| 31 | superior oblique attachment site |
| 32 | medial rectus attachment site |
| 33 | lateral rectus attachment site |
| 34 | inferior rectus attachment site |
| 35 | inferior oblique attachment site |
| 36 | outer surface |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A total ocular replacement comprising:
   a) an implant body that includes an outer surface, and comprising a spherically shaped portion with a forwardly positioned cell ingrowth surface at least on the spherical portion that is receptive of ocular conjunctiva tissue;
   b) a conformer having a rear concave surface that is shaped to conform generally to the spherical implant body and to conjunctival tissue attaching to the cell ingrowth surface of the implant body;
   c) wherein the conformer rear concave surface has a peripheral portion that extends over the ingrowth surface and the surface is shaped to interface with the combination of the implant body and attached conjunctival tissue without substantial damage to the said attached conjunctival tissue;
   d) the implant having a porous muscle ingrowth material that covers a portion of the implant body outer surface and including a plurality of muscle attachment sites for attaching a plurality of ocular muscles to the spherical implant body at spaced locations; and
   e) said outer surface having regions devoid of ingrowth material to discourage muscle attachment.

2. The total ocular implant of claim 1 wherein the body includes a forwardly extending post member and further comprising connection means for forming a removable connection between the post and the conformer at rear concave surface of the conformer, and the tissue ingrowth surface is positioned on the innermost portion of the post, and on the implant body adjacent the post.

3. The total ocular implant of claim 2 wherein the connection means includes magnetically attracted members disposed respectively in the conformer and in the implant body and in a position that prevents substantial tissue ingrowth between the magnetically attracted members.

4. The total ocular implant of claim 1 wherein the implant body is polymeric.

5. The total ocular implant of claim 2 wherein the implant body is integrally constructed to include the spherically shaped portion and the post.

6. The total ocular implant of claim 2 wherein the post includes a cellular ingrowth surface thereon.

7. The total ocular implant of claim 6 wherein the post is cylindrically shaped.

8. The total ocular implant of claim 1 wherein there are at least four (4) spaced apart muscle attachment sites on the implant body, each spaced away from the conjunctival tissue attachment site.

9. The total ocular implant of claim 1 wherein the muscle attachment sites are a porous polymeric material.

10. The total ocular implant of claim 1 wherein the prosthesis body is polymethyl methacrylate.

11. The total ocular implant of claim 1 wherein the spherical portion is of a silicone material.

12. The total ocular implant of claim 1 wherein the prosthesis body is of a synthetic polymer material.

13. The total ocular implant of claim 1 wherein the muscle attachment sites are a cubic array of micropillared polymer.

14. The total ocular implant of claim 9 wherein the pore size is at least twenty (20) microns.

15. The total ocular implant of claim 13 wherein the cubic array of micropillars is at least twenty (20) microns.

16. The total ocular implant of claim 1 wherein the muscle attachment surfaces are polyurethane.

17. The total ocular implant of claim 1 wherein the muscle attachment surfaces are polyester.

18. The total ocular implant of claim 1 wherein the muscle attachment surfaces are polytetrafluoroethylene.

19. The total ocular implant of claim 18 wherein the muscle attachment surfaces are woven polytetrafluoroethylene.

20. The total ocular implant of claim 1 wherein the muscle attachment surfaces are expanded polytetrafluoroethylene.

21. The total ocular implant of claim 1 wherein the muscle attachment sites are silicone.

22. The total ocular implant of claim 2 wherein the post is of a polymeric material.

23. The total ocular implant of claim 22 wherein the post is of a polymethylmethacrylate.

24. A total ocular replacement comprising:
a) an implant body that includes an outer surface, and comprising a spherically shaped portion with a forwardly positioned cell ingrowth surface at least on the spherical portion that is receptive of ocular conjunctival tissue;
b) a conformer having a concavely shaped rear surface; and
c) wherein the conformer concavely shaped rear surface has a peripheral portion that extends over the ingrowth surface and the concave surface is shaped to interface with the combination of the implant body and attached conjunctival tissue and without substantial damage to the said attached conjunctival tissue.

25. The total ocular implant of claim 24 wherein the body includes a forwardly extending post member and further comprising connection means for forming a removable connection between the post and the conformer at rear concave surface of the conformer, and the tissue ingrowth surface is positioned on the portion of the post, and on the implant body adjacent the post.

26. The total ocular implant of claim 24 wherein the connection means includes magnetically attracted members disposed respectively in the conformer and in the implant body and in a position that prevents substantial tissue ingrowth between the magnetically attracted member.

27. The total ocular implant of claim 24 wherein the implant body is polymeric.

28. The total ocular implant of claim 24 wherein the implant body is integrally constructed to include the spherically shaped portion and the post.

29. The total ocular implant of claim 24 wherein the post is cylindrically shaped.

30. The total ocular implant of claim 24 further comprising a plurality of muscle attachment sites on the implant body, each spaced away from the conjunctival tissue attachment site.

31. The total ocular implant of claim 30 wherein the plurality of muscle attachment sites are a porous polymeric material.

32. The total ocular implant of claim 24 wherein the prosthesis body is polymethyl methacrylate.

33. The total ocular implant of claim 24 wherein the spherical portion is of a silicone material.

34. The total ocular implant of claim 24 wherein the prosthesis body is of a synthetic polymer material.

35. The total ocular implant of claim 30 wherein the muscle attachment sites are a cubic array of micropillared polymer.

36. The total ocular implant of claim 31 wherein the pore size is at least twenty (20) microns.

37. The total ocular implant of claim 35 wherein the cubic array of micropillars is at least twenty (20) microns.

38. The total ocular implant of claim 30 wherein the muscle attachment sites are polyurethane.

39. The total ocular implant of claim 30 wherein the muscle attachment sites are polyester.

40. The total ocular implant of claim 30 wherein the muscle attachment sites are polytetrafluoroethylene.

41. The total ocular implant of claim 30 wherein the muscle attachment sites are woven polytetrafluoroethylene.

42. The total ocular implant of claim 30 wherein the muscle attachment sites are expanded polytetrafluoroethylene.

43. The total ocular implant of claim 30 wherein the muscle attachment sites are silicone.

44. The total ocular implant of claim 25 wherein the post is of a polymeric material.

45. The total ocular implant of claim 44 wherein the post is of a polymethylmethacrylate.

* * * * *